US010262423B2

(12) United States Patent
Pathak et al.

(10) Patent No.: US 10,262,423 B2
(45) Date of Patent: Apr. 16, 2019

(54) DISEASE AND FALL RISK ASSESSMENT USING DEPTH MAPPING SYSTEMS

(71) Applicant: Verily Life Sciences LLC, Mountain View, CA (US)

(72) Inventors: Anupam J. Pathak, Mountain View, CA (US); Emre Demiralp, San Francisco, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 152 days.

(21) Appl. No.: 15/469,130

(22) Filed: Mar. 24, 2017

(65) Prior Publication Data

US 2017/0287146 A1    Oct. 5, 2017

Related U.S. Application Data

(60) Provisional application No. 62/314,811, filed on Mar. 29, 2016.

(51) Int. Cl.
*G06K 9/00* (2006.01)
*G06T 7/246* (2017.01)
(Continued)

(52) U.S. Cl.
CPC ............ *G06T 7/251* (2017.01); *A61B 5/0022* (2013.01); *A61B 5/11* (2013.01); *A61B 5/1101* (2013.01);
(Continued)

(58) Field of Classification Search
None
See application file for complete search history.

(56) References Cited

U.S. PATENT DOCUMENTS 5,573,011 A    11/1996  Felsing
8,206,325 B1 *  6/2012  Najafi ................. A61B 5/1116
                                                              600/595
(Continued)

FOREIGN PATENT DOCUMENTS

EP          19998849        12/2014
WO     WO 201302289         2/2013

OTHER PUBLICATIONS

U.S. Appl. No. 15/013,626; Ali Shoeb; filed Feb. 2, 2016.
(Continued)

*Primary Examiner* — Stephen P Coleman
(74) *Attorney, Agent, or Firm* — Christensen O'Connor Johnson Kindness PLLC

(57) ABSTRACT

An apparatus, system and process for tracking and analyzing target person movements, captured while the target person is performing ordinary tasks outside of a medical context, for medical diagnosis and treatment review are described. The method may include constructing a model of a target person from three-dimensional (3D) image data of the target person performing an activity over a period of time. The method may also include tracking movement of the model of the target person in the 3D image data over the period of time, and detecting one or more motion features in the movement of the model of the target person that are relevant to diagnosis, treatment, care, or a combination thereof, of a potential chronic neurodegenerative or musculoskeletal medical condition. The method may also include computing a risk score associated with likelihood of the target person having the medical condition based on the detected motion features.

23 Claims, 9 Drawing Sheets

(51) Int. Cl.
*A61B 5/11* (2006.01)
*A61B 5/00* (2006.01)
*G16H 15/00* (2018.01)
*G06T 7/00* (2017.01)

(52) U.S. Cl.
CPC .......... *A61B 5/4082* (2013.01); *A61B 5/7275* (2013.01); *G06K 9/00348* (2013.01); *G06T 7/0016* (2013.01); *G16H 15/00* (2018.01); *G06T 2207/10016* (2013.01); *G06T 2207/10028* (2013.01); *G06T 2207/20081* (2013.01); *G06T 2207/30196* (2013.01)

(56) References Cited

U.S. PATENT DOCUMENTS

| | | | |
|---|---|---|---|
| 8,702,629 B2 | 4/2014 | Giuffrida et al. | |
| 2011/0129129 A1* | 6/2011 | Avinash | A61B 5/04 |
| | | | 382/128 |
| 2011/0313788 A1* | 12/2011 | Amland | G06Q 50/22 |
| | | | 705/3 |
| 2014/0303508 A1 | 10/2014 | Plotnik-Peleg et al. | |
| 2014/0378439 A1* | 12/2014 | Dezso | C12Q 1/6883 |
| | | | 514/215 |
| 2016/0147959 A1* | 5/2016 | Mariottini | G06N 5/02 |
| | | | 706/46 |

OTHER PUBLICATIONS

Horak, F.B. et al., "Postural Strategies Associated with Somatosensory and Vesitbular Loss," *Experimental Brain Research*, Feb. 22, 1990; 82:167-177.

Baston, Chiara et al., "Postural Strategies Assessed with Inertial Sensors in Healthy and Parkinsonian Subjects," *Gait & Posture*, Feb. 20, 2014; 1-6.

* cited by examiner

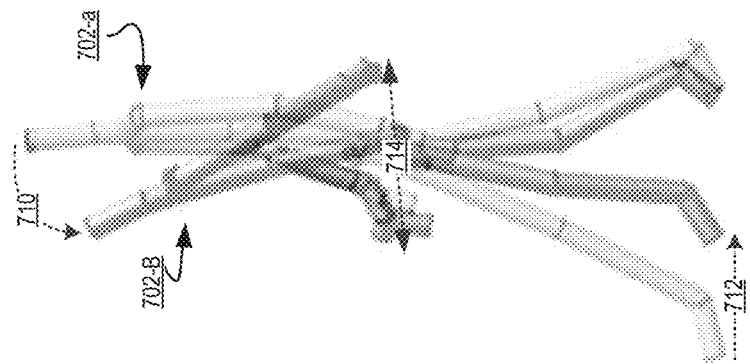
FIG. 7C
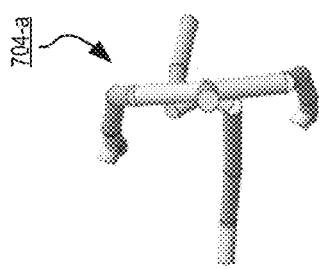
FIG. 7A
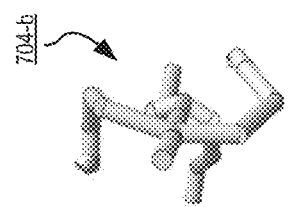
FIG. 7B
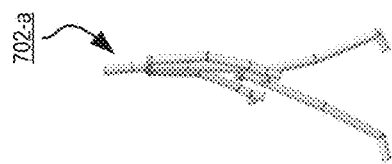

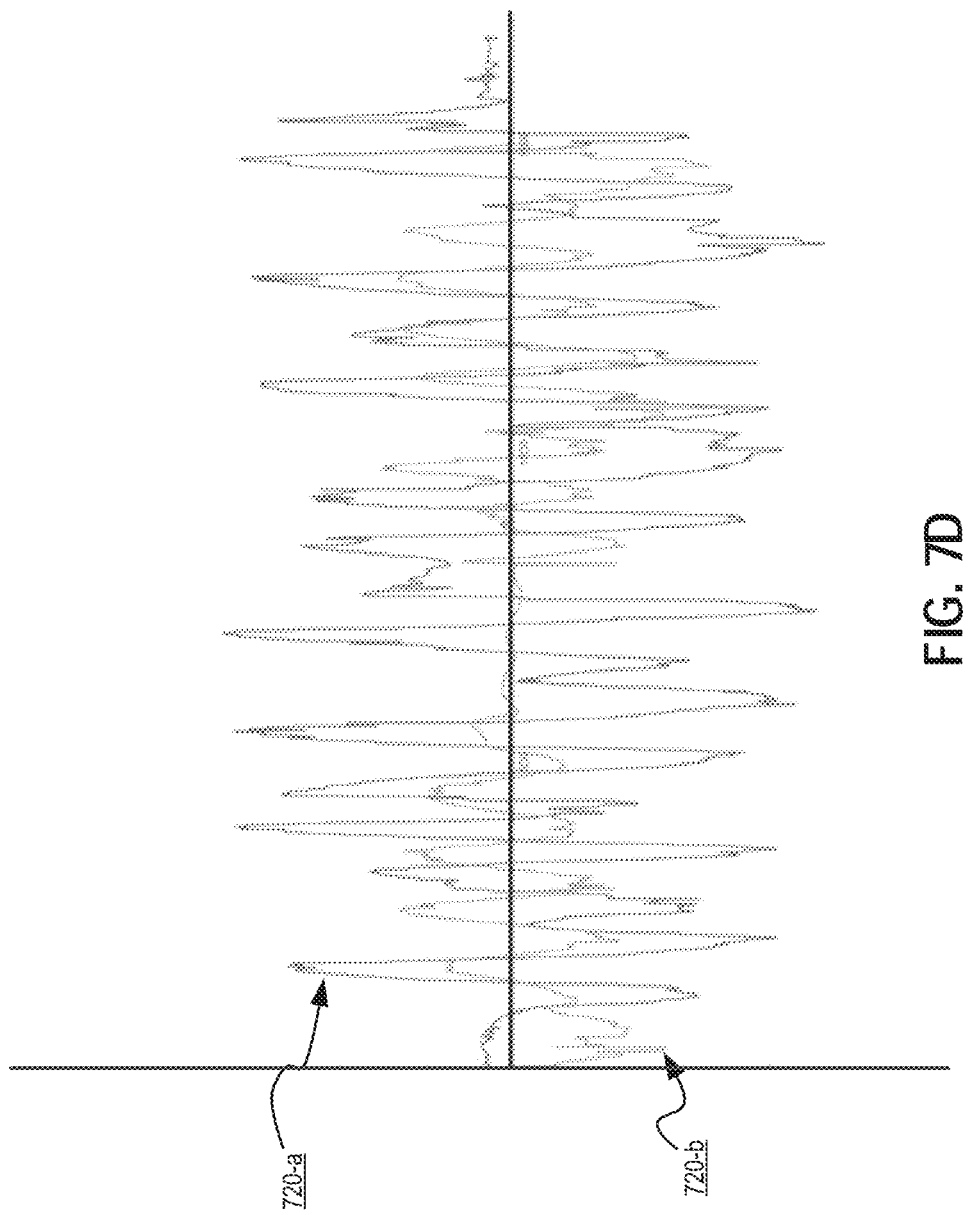

US 10,262,423 B2

DISEASE AND FALL RISK ASSESSMENT USING DEPTH MAPPING SYSTEMS

PRIORITY

The present patent application claims priority to and incorporates by reference the corresponding provisional patent application Ser. No. 62/314,811, titled, "Disease and Fall Risk Assessment Using Depth Mapping Systems" filed on Mar. 29, 2016.

FIELD

This disclosure relates generally to tracking user movements for medical treatment and diagnosis, and in particular but not exclusively, relates to the measurement and tracking of user movements using a depth mapping systems.

BACKGROUND INFORMATION

Movement disorders are often caused by chronic neurodegenerative diseases such as Parkinson's Disease ("PD") and Essential Tremor ("ET"). Both of these conditions are currently incurable and cause unintentional muscle movements or human tremors—uncontrollable rhythmic oscillatory movements of the human body. In many cases human tremors can be severe enough to cause a significant degradation in quality of life, interfering with daily activities/tasks such as eating, drinking, or writing.

Patients with movement disorders are typically diagnosed in a clinic using scales such as the Fahn-Tolosa-Marin Tremor Rating Scale for ET or the Unified Parkinson Disease (UPDRS) rating scale for PD. Both of these scales require a trained neurologist to complete and often rely on subjective assessments that occur over a brief period of time in the practitioner's office. Symptom severity at home is typically evaluated from the patient's self-reporting, which is also highly subjective and prone to error. Some devices have been used to track lower extremity freezing, but require bulky and obtrusive sensors that a user must wear. This creates significant challenges when diagnosing, developing and evaluating long-term treatments or interventions for these diseases.

BRIEF DESCRIPTION OF THE DRAWINGS

Non-limiting and non-exhaustive embodiments are described with reference to the following figures, wherein like reference numerals refer to like parts throughout the various views unless otherwise specified. The drawings are not necessarily to scale, emphasis instead being placed upon illustrating the principles being described.

FIG. 7A illustrates embodiments of different views of a healthy user during a walking motion.

FIG. 7B illustrates embodiments of different views of a user having a chronic neurodegenerative disease during a walking motion.

FIG. 7C illustrates a comparison of postural and motion differences of the healthy user and the user having the chronic neurodegenerative disease during the walking motion.

FIG. 7D illustrates quantified stride length and stride frequency of a health user and a user with a chronic neurodegenerative disease.

DETAILED DESCRIPTION

Figure 1:
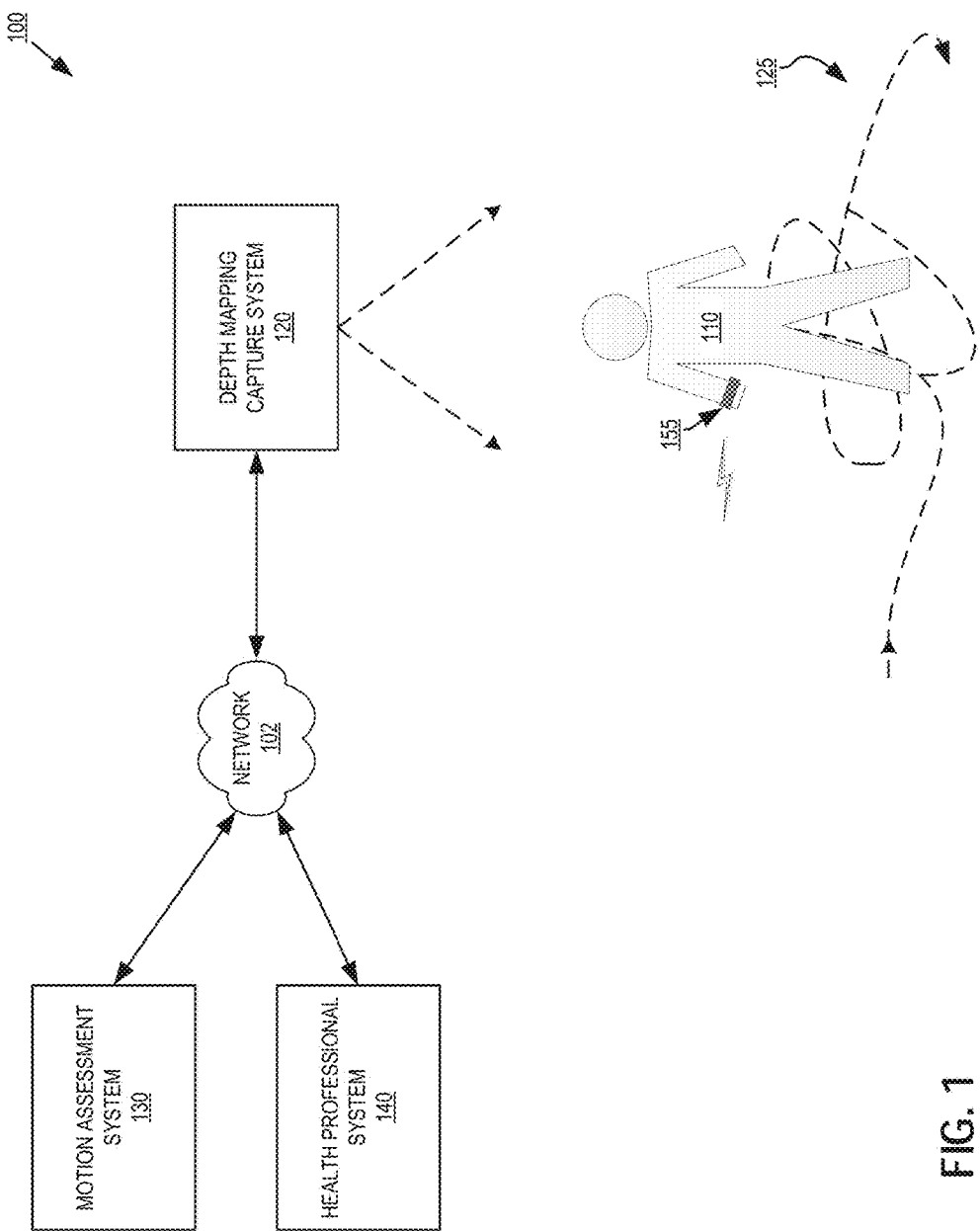
FIG. 1 is a block diagram of an exemplary system architecture for tracking and analyzing user movements for medical treatment and diagnosis using a depth sensor.

Embodiments of an apparatus, system, and process for tracking and analyzing user movements using depth sensor data, captured while the user is performing ordinary tasks outside of a medical context, for medical diagnosis and treatment review are described herein. In embodiments, a motion capture system is utilized to capture three dimensional motions of the user while the user is performing everyday activities, such as walking, eating, sitting, standing, etc. Furthermore, the motion capture system can be deployed anywhere, such as in a user's home where he or she is most comfortable. In embodiments, the motion capture system can include a depth mapping sensor system for capturing three-dimensional image data of user motions. However, other forms of motion capture, such as wearable devices having one or more sensors, motion sensors affixed to specific locations of a user's body, access point location information, etc. may be used to capture three-dimensional user motion data.

In embodiments, the three-dimensional motions of the user are compared with one or more motion models by a motion analysis system. In embodiments, the motion models correspond with models generated from people known to have a chronic neurodegenerative (e.g., PD, ET, etc.) or a musculoskeletal (e.g., spinal dysfunction) condition. However, other motions models, such as those trained by machine learning, a model generated from the user's own motions, etc. may also be used. Based on the model comparison, such as determining a similarity between captured user motions and motions in a specific model, the motion assessment system can detect motion features in the user's model that are relevant to the diagnosis, treatment, care, or a combination thereof, of a potential chronic neurodegenerative or musculoskeletal medical condition. Furthermore, certain motions (e.g., tremor motions, freezing, etc.), when detected and based on their similarity to corresponding model motions, enable the motion analysis system to further determine a risk score related to the diagnosis or treatment of a medical condition In the embodiments discussed herein, the problems associated with traditional diagnostic approaches, such as subjectivity of a medical professional, a patient being unable to perform certain motions, a patient being uncomfortable in a diagnosis context thereby affecting how motions are performed, a patient being fatigued during examination leading to a deterioration in motions, certain motions being undetectable by the human eye, etc. are eliminated since the user motions can be captured and analyzed at any time and in environments in which a user is comfortable. Furthermore, the period of motion capture from which a diagnosis may be made need not be limited to a single visit to a medical professional, as continued motion capture, analysis, and diagnosis can be performed as discussed herein. Thus, the systems and techniques described herein enable a greater diagnostic data set, which more accurately reflects a user's actual motions, from which the motion analysis discussed herein can be performed.

In the following description, numerous details are set forth. It will be apparent, however, to one of ordinary skill in the art having the benefit of this disclosure, that the embodiments discussed herein may be practiced without these specific details. In some instances, ell-known structures and devices are shown in block diagram form, rather than in detail, in order to avoid obscuring the embodiments discussed herein.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical signals, magnetic signals, other signals, or combinations thereof that are capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "capturing", "constructing", "tracking", "detecting", "comparing", "monitoring", "initiating", "performing", "communicating", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Some embodiments relate to an apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings described herein.

FIG. 1 is a block diagram of an exemplary system architecture 100 for tracking and analyzing user movements for medical treatment and diagnosis using a depth sensor. In embodiments, the system includes a depth mapping capture system 120 and a motion assessment system 130. The system may also include a health professional system 140. In embodiments, depth mapping capture system 120 may be a computer processing system, such as a personal computer, video game console, computing appliance, etc., coupled with a depth mapping sensor, such as a three-dimensional motion capture system. The motion assessment system 130 and health professional system 140 may also be computing devices, such as one or more server computers, desktop computers, etc.

The depth mapping capture system 120, motion assessment system 130, and health professional system 140 may be coupled to a network 102 that communicates using any of the standard protocols for the exchange of information. In embodiments, depth mapping capture system 120 is coupled with network 102 via a wireless connection, such as a wireless fidelity connection, etc. The depth mapping capture system 120, motion assessment system 130, and health professional system 140 may run on one Local Area Network (LAN) and may be incorporated into the same physical or logical system, or different physical or logical systems. Alternatively, the depth mapping capture system 120, motion assessment system 130, and health professional system 140 may reside on different LANs, wide area networks, cellular communication networks, etc. that may be coupled together via the Internet but separated by firewalls, routers, or other network devices. It should be noted that various other network configurations can be used including, for example, hosted configurations, distributed configurations, centralized configurations, etc.

The depth mapping capture system 120 is responsible for capturing depth image data with a depth mapping sensor (not shown) of motions of user 110. The depth mapping sensor may be a three-dimensional image capture sensor, such as a depth camera sensor, an assisted depth camera sensor, etc., that captures image/video data simultaneously from multiple cameras of known relative orientations, and extrapolates depth information from the different captured images. Furthermore, the depth mapping sensor may be an assisted sensor, such as those that project a three-dimensional infrared pattern and utilize an infrared camera to capture depth information from the projected pattern. In any of these embodiments of the depth mapping sensor, depth mapping capture system 120 is capable of capturing images and video of user 110 that includes depth information for the elements in the captured scene.

In embodiments, the depth information captured by depth mapping sensor system 120 is captured over a period of time as user 110 performs one or more tasks within the scene (or field of view) of the depth mapping sensor of the depth mapping sensor system 120. For example, the depth mapping sensor system 120 may capture three-dimensional depth information when a user enters a room, how long they are in the room, what tasks they are performing, etc.

Figures 6A, 6B:
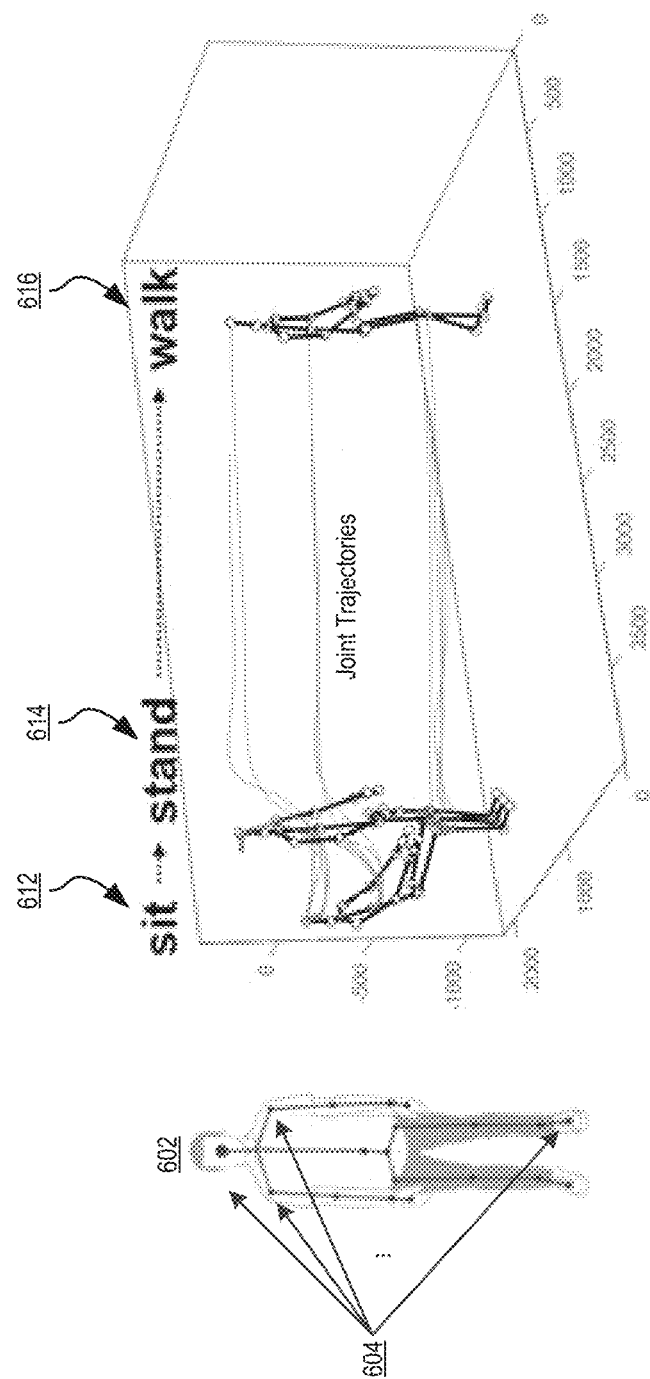
FIG. 6A illustrates one embodiment of a skeletal model of a user.
FIG. 6B illustrates on embodiment of movement of the skeletal model of the user over a period of time.

Depth mapping sensor system 120 uses the depth information to generate three-dimensional location data indicative of different parts of the user's body over a period of time. For example, from the captured depth sensor data, depth mapping sensor system 120 locates points 604 of the users body 602 (e.g., left knee, right knee, left ankle, right ankle, left shoulder, right shoulder, etc.), such as the points illustrated in FIG. 6A. Depth mapping sensor system 120 then determines the movement of those points in space over a period of time (e.g., a movement of the point from one location ($x_i, y_i, z_i, t_i$) to another location ($x_j, y_j, z_j, t_j$) over an interval of time), as well as movement of multiple identified points relative to one another, such as the movement of those points as a result of the user 602 sitting 612, standing 614, and walking 616 over a period of time, as illustrated in FIG. 6B.

In embodiments, those identified points and movement of hose points within the captured depth sensor data are a model of the user's 110 movement, with the points being nodes of the user model. The model therefore represents the structure and movement of a human body (e.g., user's 110 body). An embodiment of a visualization of the model of the user's movement over a period of time is illustrated in FIG. 6B. Another embodiment of a visualization of the model of a user is illustrated in FIG. 7A. In embodiments, depth mapping sensor system 120 tracks the model's movement over a period of time to determine the user's 110 movements over that period of time. The user movement may be captured any time the user is within the field of view of the depth mapping sensor of depth mapping sensor system 120, during specific time periods, when the motion data indicates the user is performing a specific task, as configured by a health professional, etc. In embodiments, the depth information (e.g., spatial and temporal location of tracked points of the user model) is logged by depth mapping sensor system 120, and periodically transferred to motion assessment system 130.

Some embodiments, additional user motion data, such as motion data captured by a wearable device 155 may also be captured during user movement 125. In embodiments, the wearable device 155 may be a fitness tracker, smart watch, pedometer, etc. that includes one or more sensors (e.g., accelerometers, gyroscopes, GPS, etc.) that track user movements. In embodiments, the wearable device 155 may be a plurality of different or the same wearable devices, such as wearable devices along each joint of a user, a wearable device on limbs of interests (e.g., a limb experiencing tremor symptoms), etc. In embodiments, this additional user motion data is transferred, such as by a wireless communication link, to one or more of depth mapping capture system 120 or motion assessment system 130. Time information associated with the user motion data captured by wearable device 155 is used by depth mapping sensor system 120 to correlate the different forms of motion data for transmission to motion assessment system 130. Additional motion data, such as motion data obtained from wireless transmitter signal disruption analysis, motion data from one or more assistance devices (e.g., a cane or walker tracking user motions via one or more accelerometers, an eating implement that tracks user motions, etc.), as well as other motion data may be captured for use by the motion assessment system 130, in accordance with the discussion herein. Furthermore, one or more of the additional forms of user motion data, such as that captured by wearable device 155, may be used by motion assessment system 130 to track and analyze user movements independent of the image data captured by depth mapping system 120.

Motion assessment system 130 receives the captured depth sensor data including the location data for the tracked nodes/points of the user model. The depth sensor data includes a physical location component (e.g., data indicative of an (x, y, z) location in space where a node in the model is located), and a time component (e.g., what time t is associated with the (x, y, z) location of the node). In embodiments, the motion assessment system 130 utilizes the movement of the user model data over a period of time, such as the period of the captured depth sensor data, sub-periods within the captured depth sensor data, or combined periods from different periods of captured depth sensor data.

In embodiments, as discussed above, depth mapping sensor system 120 captures depth sensor data and preprocesses the captured data by generating a user model (e.g., location and tracking of specific points associated with the user), and extracts location data associated with movement of those points. In another embodiment, depth mapping sensor system 120 may capture depth sensor data without generation of a user model (e.g., point location and extraction from depth sensor data) or tracking of the movement of those points. Instead, depth mapping sensor system 120 may transfer the captured depth sensor data (e.g., video data with depth information) to motion assessment system 130, which performs the user model generation, feature point extraction, point location, and motion tracking discussed above.

In either embodiment, motion assessment system 130 compares the movements of the user model over a period of time with movement of one or more baseline models. In embodiments, the baseline models may be models captured of users with known chronic neurodegenerative or musculoskeletal conditions. In other embodiments, the baseline models are machine learning models trained using one or more movement features of one or more people with known chronic neurodegenerative or musculoskeletal conditions, such that each trained machine learning model represents the motion patterns of an entire population of people having a chronic neurodegenerative or musculoskeletal condition. For example, FIG. 7A illustrates a side view 702-*a* of a frame of a baseline model generated from healthy user's movements while walking a given distance and a frame of a top view 704-*a* of the model, which are generated from the depth sensor data captured over a period of time by depth mapping camera system 120. FIG. 7B, however, illustrates a side view 702-*b* of a frame of a model generated from a user's movements who is afflicted with a chronic neurodegenerative or musculoskeletal disease, and a top view 704-*b* of that user's model, which are also generated from the depth sensor data captured over a period of time by depth mapping camera system 120. In embodiments, the movement of the baseline models may provide movement data for a healthy baseline (e.g., a different user who has not been diagnosed with a chronic neurodegenerative or musculoskeletal disease), for a condition specific baseline (e.g., a different user who has been diagnosed with a chronic neurodegenerative or musculoskeletal disease, a machine learning model trained by people diagnosed with a chronic neurodegenerative or musculoskeletal medical condition, etc.), and for the user's own historical baseline (e.g., the same user's movements at different periods of time). In embodiments, motion assessment system 130 compares the movement of the user model with one or more of the baseline model's movements to extract features indicative of existence of a chronic neurodegenerative or musculoskeletal disease, to track severity of symptoms of a chronic neurodegenerative or musculoskeletal disease over time, to compute a risk score indicative of a patient having or developing a chronic neurodegenerative or musculoskeletal disease, etc. For example, the motion assessment system 130 can compare tracked movements of the user model with a machine learning model trained to represent a specific chronic neurodegenerative or musculoskeletal disease when computing a risk score for a patient. Furthermore, the computation of a risk score can be performed by motion assessment system 130 in real time, as the various forms of motion data are being captured and tracked for a user.

Figure 7E:
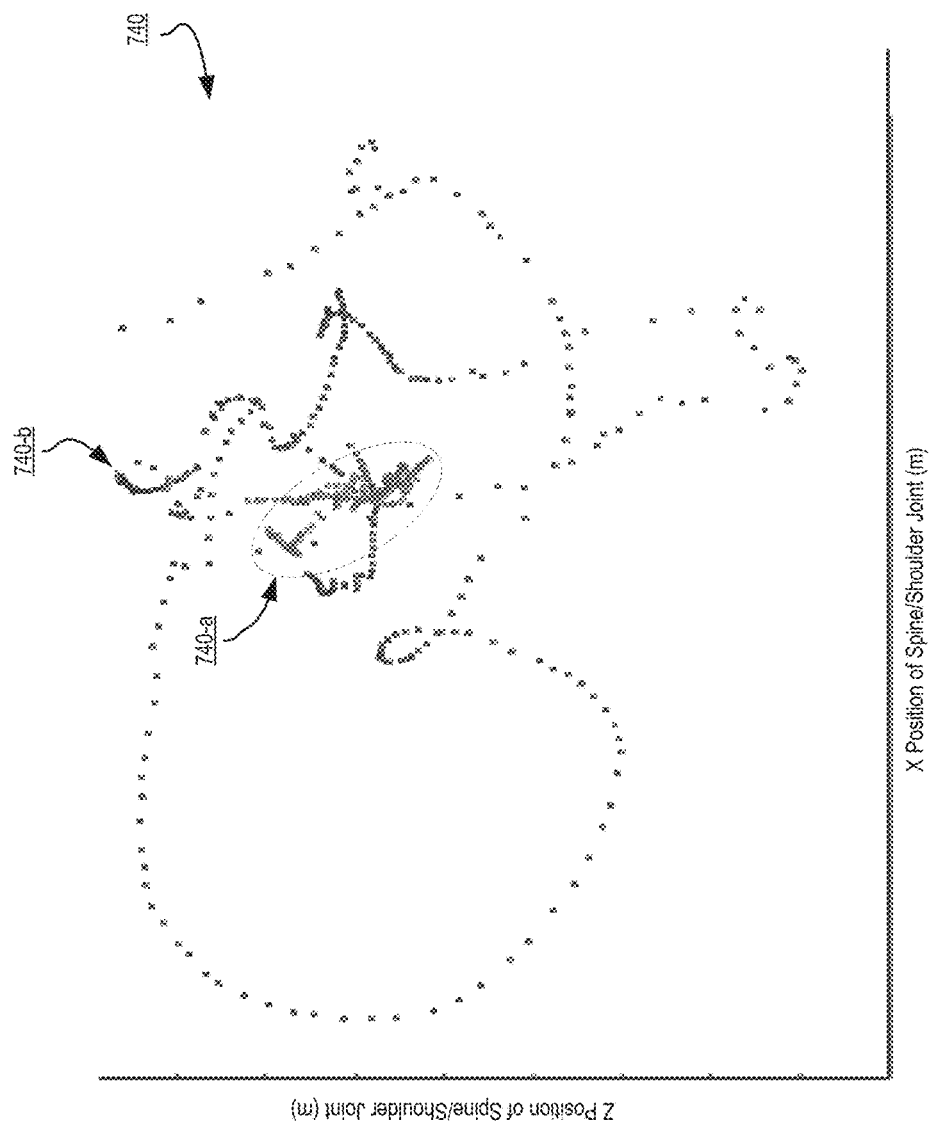
FIG. 7E illustrates quantified postural sway of a health user and a user with a chronic neurodegenerative disease.

For example, comparison of the baseline model of FIG. 7A with the model of FIG. 7B enables motion assessment system 130 to locate certain motion features relevant to the discovery and diagnosis of a chronic neurodegenerative or musculoskeletal disease, such as forward leaning posture 710, reduced stride length 712, and arm swing 714. Motion features, such as characteristic forward-leaning (e.g., stooped) posture, postural sway, diminished stride length, increased stride frequency, lack of arm sway, tremor motions, etc., are quantifiable from a skeletal model generated from user movements or based on comparison to a baseline model. For example, quantified stride length and frequency of a healthy user's model 720-*a* is illustrated in FIG. 7D. When compared to stride length and frequency of a user's model 720-*b* undergoing an assessment for a chronic neurodegenerative or musculoskeletal disease, the diminished stride length and increased stride frequency can be indicators relevant to a diagnosis or risk score for a chronic neurodegenerative or musculoskeletal disease. As another example, both amplitude and frequency of arm swing can be extracted from movements of a user's model. It is known that patients with a chronic neurodegenerative disease, such as Parkinson's Disease, keep their arms relatively still while walking, which can be quantified form the captured depth sensor data by subtracting depth coordinates of a model's wrist node in a skeletal model. Similarly, an increase in frequency of arm swing of a model generated from user movements above a baseline model's arm swing may also be an indicator of a chronic neurodegenerative disease. As yet another example, postural sway observed in a user who is sitting in a chair, standing, or otherwise in a resting position, asked to make a movement (e.g., standing from the chair), and then attempts to remain motionless, is another indicator of a chronic neurodegenerative disease that can be captured and quantified using depth sensor data. FIG. 7E illustrates X and Z position (e.g., left/right and to/from the depth mapping capture system 120) of a user model's shoulder/spine showing a significant difference in a health user's sway 740-*a* and the sway 740-*b* of a user undergoing diagnosis for a chronic neurodegenerative disease. Other motions, such as walking motions, arm motions, posture, etc. may also be analyzed when, for example, a user is using an assistance device (e.g., a cane, walker, etc.), when interacting with another individual, or any other user motion relevant to the detection or diagnosis of a chronic neurodegenerative disease. Each of these motions may be used to adaptively score a user's risk for having one or more chronic neurodegenerative or musculoskeletal diseases, a risk of falling as a result of one of the chronic neurodegenerative or musculoskeletal diseases, as well as other risk factors associated with chronic neurodegenerative or musculoskeletal diseases.

In embodiments, the postural, stride, arm swing motions, or a combination of motion characteristics analysis can be performed by comparison to healthy models and detecting a deviation from corresponding characteristics in the healthy model beyond a threshold amount. In another embodiment, postural, stride, arm swing, or a combination of motion characteristics analysis can be performed by comparison to specific models generated from user diagnosed with one of a plurality of chronic neurodegenerative or musculoskeletal disease to distinguish between different potential chronic neurodegenerative or musculoskeletal diseases afflicting a user. In yet another embodiment, postural, stride, arm swing, or a combination of motion characteristics analysis can be performed by comparison to a model generated from a user's prior motions in order to analyze trending of a chronic neurodegenerative or musculoskeletal disease over time, whether treatment is working, and update one or more risk scores.

In some embodiments, however, movements of the user's model may be analyzed without reference to a baseline model. For example, the movements of the user model may be analyzed to detect user movement features, such as arm swing, stride length, stride frequency, pace, postural sway, etc., having a predetermined value that is associated with a chronic neurodegenerative or musculoskeletal disease (e.g., stride length below a threshold length, postural sway beyond a threshold distance, arm swing below a threshold distance, etc.). Furthermore, because the movement data includes temporal information, the detected user movement features may also be tracked over time to detect user fatigue, as indicated by decreased stride length, decreased stride frequency, etc. Additionally, certain motion feature, such as freezing, tremor, etc. may also be detected from the movements of the user model.

For embodiments, motion assessment system 130 may be communicably coupled with a health professional system 140. In embodiments, following consent of user 110, a health professional providing diagnosis, treatment, and care for a patient with a potential chronic neurodegenerative or musculoskeletal disease to user 110 may receive reports of the user's movements. The reports may include extracted features indicative of a new chronic neurodegenerative or musculoskeletal medical disease, trending analysis of an existing chronic neurodegenerative or musculoskeletal disease, adaptive risk scoring based selected features and trending motion analysis of those features, and other features relevant to detection, treatment, and care for a chronic neurodegenerative or musculoskeletal disease. The reports, in embodiments, may generate a visualization of the captured user movements 125 using the user model's movement, such as one or more of the visualizations illustrated in FIGS. 6B and 7A-7E. The medical practitioner is therefore provided with the analysis results regarding the features extracted from the depth sensor data indicative of the chronic neurodegenerative or musculoskeletal disease, and can view of a visualization for further analysis purposes.

For embodiments, health professional system 140 enables a medical practitioner to input data relevant to the detection, treatment, and care for a chronic neurodegenerative or musculoskeletal disease, such as data indicative of starting medication, ending a medication, changing a medication dosage, physical therapy, neural stimulation, dosage reports from smart medicine bottles, prescribed diet, prescribed activity, etc. In embodiments, motion assessment system 130 utilizes the inputted information when performing user model motion analysis to detect trends relevant to the start, stop, or adjustment of a specific treatment or medication. Furthermore, various detected treatment events (e.g., the inputted data) can be used to adjust previously computed risks scores, and when computing new risk scores, for a user. In embodiments, responsive to one or more detected treatment events, motion assessment system 130 can measure a treatment response, such as through 3D motion analysis of one or more motion features (e.g., through comparison to a trained machine learning motion model, comparison to one or more baseline models, etc.), by comparison of motion features to one or more thresholds (e.g., stride length threshold, stride frequency, arm swing characteristics, posture sway characteristics, frequency of freezing events, etc.), etc. Alternatively, a health professional may enter a treatment event response. The motion assessment system 130 may then adjust how a risk score associated with a user is computed, such as by one or more of adjusting one or more motion characteristic thresholds, changing a machine learning model from which a risk score is computed, changing coefficients or parameters of the risk score computation to account for the treatment, changing coefficients or parameters of the risk score computation based on the measured response to the treatment event, etc. For example, motion assessment system 130 may detect motion features indicative of PD, and then receive input from a medical practitioner that user 110 has started a new medication. The motion assessment system 130 may then provide a trend analysis of the motion features indicative of PD from the start of the new medication and determine effectiveness of the new medication relevant to the PD, and adapt risk scores to reflect the new medication. In embodiments, the reports or visualization enable a medical practitioner treating user 110 to monitor ongoing treatments, adjust existing treatments based on captured real world movements of the user, determine how existing treatments will impact a risk score associated with a neurodegenerative or musculoskeletal condition, start new treatments based on diagnosis of a new condition and/or to lower a risk score, as well as to take other actions based on the received reports and motion visualizations.

In embodiments, more than one depth mapping sensor system 120 may be used to capture different depth sensor data of user 110. For example, each room of a user's home, different scenes within the same room, different physical locations (e.g., at the user's home 110 and a practitioner's office) may include a depth mapping sensor system, and each depth mapping sensor system transfers captured depth sensor data to motion assessment system 130. Motion assessment system 130 may combine the depth sensor data motion analysis from the different depth sensor data to gain a fuller picture of the user's 110 movements, such as locating different condition triggers based on location, task, etc. captured by the different depth mapping sensor systems.

In embodiments, depth mapping sensor system 120 may be utilized to capture depth sensor data of different users, simultaneously or at different times. For some embodiments, depth mapping sensor system 120 distinguishes between different users, such as by utilizing facial recognition, locating distinguishing characteristics, based on a glyph or other marking work by different users, etc. Then, depth mapping sensor system 120 may store motion data, generate different models, track the models, etc. for the different users consistent with the discussion herein. Furthermore, the movements of the different user may be relevant one or more movements of a user's model when detecting how user's movements are effected by different scenarios (e.g., how a user's motion changes when certain individuals are present, how a user's motion changes relative to movements of other users over time, etc.).

Furthermore, in embodiments, motion assessment system 130 may be included in depth mapping capture system 120. In such embodiments, the computing device at the location of the user 110 would provide the motion analysis, interface for the health professional system 140, and the generation of reports as discussed herein.

Figure 2:
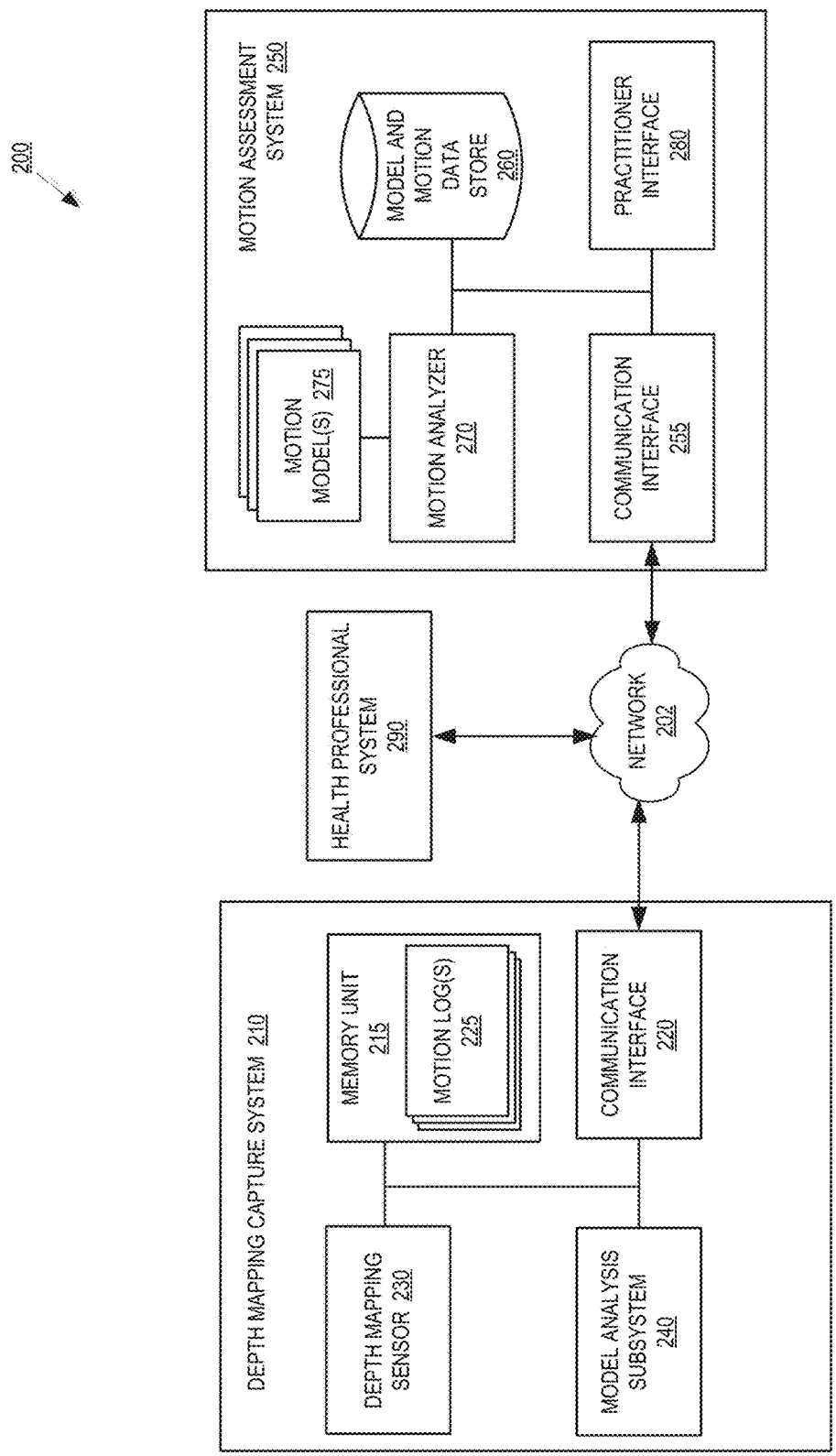
FIG. 2 is a block diagram of an embodiment of a depth mapping capture system and a motion assessment system.

FIG. 2 is a block diagram of an embodiment 200 of a depth mapping capture system and a motion assessment system. Depth mapping capture system 210 and motion assessment system 250 provide additional details for the depth mapping capture system 120 and motion assessment system 130 discussed above in FIG. 1.

In embodiments, the depth mapping capture system 210 includes a depth mapping sensor 230, a model analysis subsystem 240, a memory unit 215 to store motion log(s) 225, and a communication interface 220. In embodiments, the motion assessment system 250 includes a communication interface 255, a motion analyzer 270, one or more motion model(s) 275, a practitioner interface 280, and a model and motion data store 260. In embodiments, the depth mapping capture system 210 and motion assessment system 250 communicate with each other over various networks 202 and network configurations as discussed above in FIG. 1.

The depth mapping capture system 210, in embodiments, can be implemented in a computing device, such as a desktop computer, laptop computer, tablet computer, computing appliance, video game console, as well as other computing devices. Depth mapping sensor 230 of depth mapping capture system 210 is responsible for capturing depth imaging data (e.g., still or video data) with three-dimensional depth information for the objects captured within a scene. In some embodiments, the captured depth video data of the scene includes a user and movement of the user while the user is performing ordinary tasks. As discussed herein, the depth mapping sensor 230 may be a multi-camera depth camera system, which utilizes the known fixed location of the cameras (and optional infrared projector), to extrapolate depth information for objects within captured video data. The depth mapping sensor 230, however, need not be limited to multi-camera systems, as any depth mapping sensor providing user location data as discussed herein may be utilized by depth mapping capture system 210.

Depth mapping sensor 230 stores the captured depth sensor data (e.g., video data with depth information) in the memory unit 215. Memory unit 215 may be implemented using volatile or non-volatile memory (e.g., flash memory). In embodiments, since depth mapping sensor 230 captures depth sensor data over a period of time, as discussed herein, the stored depth sensor data is associated with time information indicative of when the data was captured, such as with a timestamp.

In embodiments, model analysis subsystem 240 may preprocess the captured depth sensor data prior to communication with the motion analysis system 250. In such embodiments, model analysis subsystem 240 analyzes the captured depth sensor data to create a skeletal model for a user within the captured depth sensor data. In embodiments, the skeletal model includes nodes/points located on the user that correspond to the user's joints (e.g., left knee, right knee, left ankle, right ankle, left wrist, right wrist, etc.). One example of a skeletal model is illustrated in FIG. 6A. In embodiments, the skeletal model is generated by model analysis subsystem 240 using computer vision techniques. In embodiments, the information associated with the motion data (stored in memory unit 215) is used by model analysis subsystem 240 to correlate the nodes/points of the skeletal model in the depth sensor data with a movement of those nodes/points over time, as illustrated by FIG. 6B showing movement of the skeletal model of FIG. 6A. That is, the difference in location of the nodes/points of the skeletal model at different points in time (e.g., $(x_i, y_i, z_i, t_i)$ and $(x_j,$ $y_j$, $z_j$, $t_j$)) indicate movement of the nodes/points, and when movement of all nodes/points is accounted for, the motion of the user model as a whole can be tracked.

In embodiments, the tracked motion data of the generated user model is stored in motion log(s) 225, and periodically transferred to motion assessment system 250 via communication interfaces 220 and 255. The received tracked motion data of the generated user model is stored in model and motion data store 260.

Motion analyzer 270 accesses the motion data for a user model to detect one or more characteristics of the user motion. These characteristics could be characteristics indicate of PD, essential tremor, spinal dysfunction, or other chronic neurodegenerative or musculoskeletal disease. In embodiments, the characteristics can be located within the motion data through simulation of the motion and feature extraction (e.g., identification of specific periodic movements at specific frequencies of the user model, identification of sudden halts in movements (i.e., freezing) not associated with halts in other locations of a user model, identification of falling events, etc.). In some embodiments, motion analyzer 270 utilizes one or more motion model(s) 275 for comparison with motion of a user's model. That is, the motion model(s) 275 can include models of motion associated with a chronic neurodegenerative or musculoskeletal disease (e.g., a condition specific baseline), model(s) of motion associated with a healthy patient (e.g., a healthy/control baseline), and model(s) of prior user motions (e.g., a user-specific baseline). In embodiments, image or motion tracking and recognition detects a similarity between the movement of the stored user model (e.g., from store 260) with one or more of the motion models 275. When a similarity is found, such as within a certain confidence interval of similarity, the motion of the user's model can be correlated with a condition associated with the identified motion model 275 and a risk score indicative of the user having or developing a chronic neurodegenerative or musculoskeletal medical condition determined therefrom. Furthermore, when a user-specific model is used, time based trend analysis, medical treatment history, new medications, adjusted medications, etc. can be analyzed to determine if a user's previously identified condition is being maintained, improving, worsening, etc., and refining or adapting a previously computed risk score.

In embodiments, practitioner interface 280 enables health professional system 290 to input patient specific information for which a patient has given authorization into model and motion data store 260. The patient specific information can include, for example, a date when a new medication was started, a date when a new physical therapy treatment was started, diagnosis of a chronic neurodegenerative or musculoskeletal medical condition, as well as other treatment, diagnosis, and care indicators. In embodiments, motion analysis system 270 can access patient specific information to select between motion model(s) 275 when doing motion analysis. Furthermore, motion analysis system 270 can access patient specific information in order track an increase or decrease in a motion feature (e.g., tremor, stride frequency, rate of fatigue, spinal dysfunction, etc.) associated with a chronic neurodegenerative or musculoskeletal medical condition over time, relative to a new treatment, diagnosis, medication, dosage change of an existing medication, based on estimated levels of a medication in the patient's bloodstream during motion, specific medical indicators, medical test assessment, adapt one or more risk scores, etc.

Motion analyzer 270 stores the analysis results in store 260. The analysis results may be accessed by practitioner interface 280 on a periodic or on-demand basis in order to generate reports for the health professional system 290. In embodiments, the reports indicate the features detected during analysis of the motion of the user's skeletal model, such as features indicative of existence of a chronic neurodegenerative or musculoskeletal disease. These features can include frequency of tremors/freezing, frequency of occurrence, magnitude of specific events, specific motion characteristics (e.g., postural sway, stride length, arm movement, etc.), as well as other extracted motion features relevant to the diagnosis or treatment of a chronic neurodegenerative or musculoskeletal disease. The reports can also indicate a trend analysis of a specific feature over a period of time, or in view of a new factor (e.g., new medication, medication dosage change, treatment change, newly diagnosed condition, etc.). Furthermore, the reports can make an assessment of the patient, such as a fall risk assessment based on gait, balance, stride, tremor, sway, detected falls, as well as other detected motion features. Trending analysis of the motion of the user may also be used to assess the level of risk, such as high, low, oderate, etc. based on the detected trending or existence of certain motion features.

Figure 3:
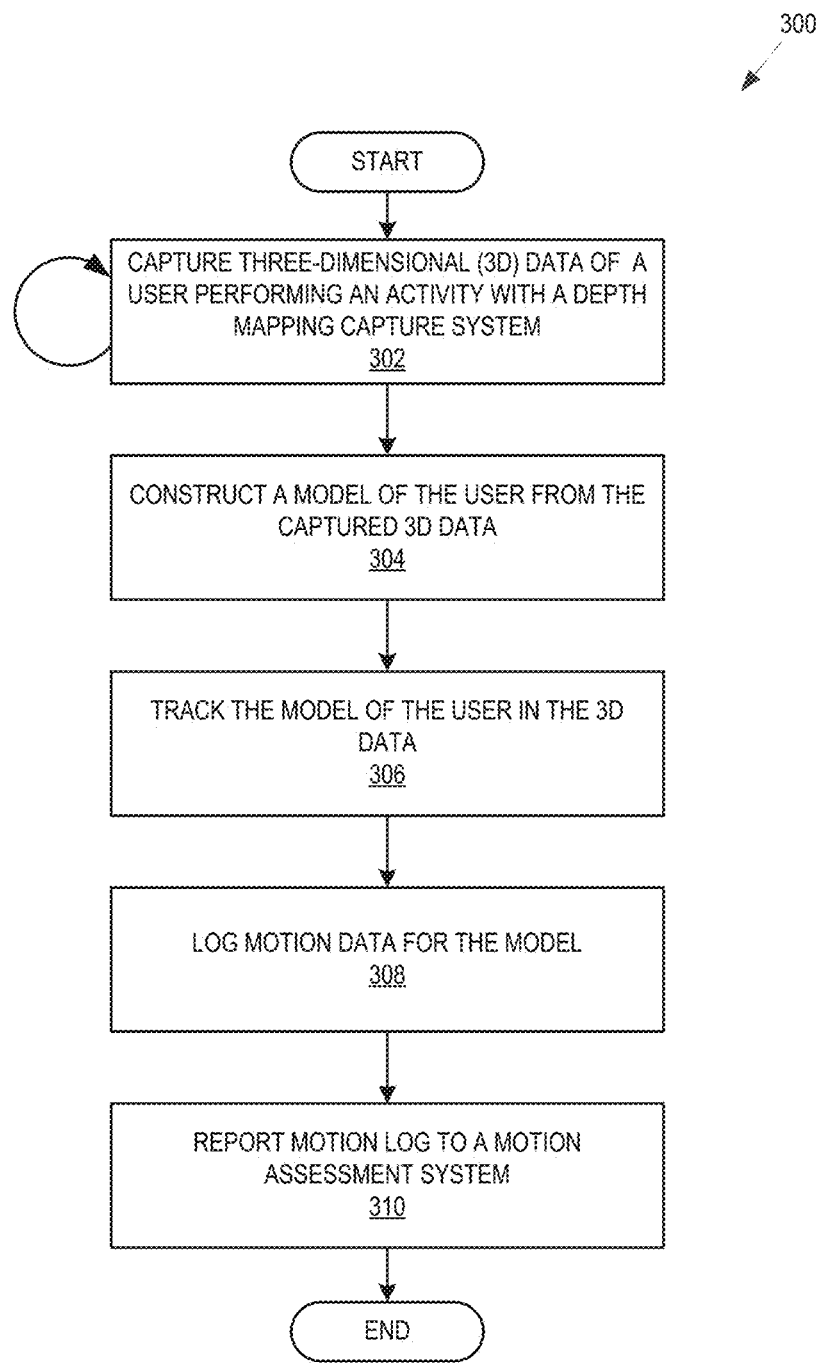
FIG. 3 is a flow chart illustrating a process for collecting and modeling user movements at depth mapping capture system, in accordance with an embodiment of the disclosure.

FIG. 3 is a flow chart illustrating a process 300 for collecting and modeling user movements at depth mapping capture system, in accordance with an embodiment of the disclosure. The process is performed by processing logic that may comprise hardware (circuitry, dedicated logic, etc.), software (such as is run on a general purpose computer system or a dedicated machine), firmware, or a combination. In embodiments, the process is performed by a depth mapping capture system (e.g., depth mapping capture system 120 or 210).

Referring to FIG. 3, processing logic begins by capturing three-dimensional (3D) data of a user performing an activity with a depth mapping capture system (processing block 302). In embodiments, the user can be considered as a target person whose motions will be analyzed for diagnosis or treatment of a chronic neurodegenerative or musculoskeletal condition. In embodiments, the three-dimensional data may be depth sensor data and includes a plurality of frames of image data (e.g., a video). Alternatively, the three dimensional data may be acceleration measurements captured by one or more wearable devices, access point signal disruption data, or another type of three dimensional data indicative of user movements. In embodiments, the three dimensional data may include a combination of any of the different types of three dimensional data. The three-dimensional data is captured over a period of time to capture motion of the user while the user is performing ordinary activities, such as walking, performing household chores, eating, etc. outside of a medical context. By utilizing the depth mapping capture system, as well as the other systems for capturing motion data, the user motion data is captured in a non-invasive way that will not impact how the activity is performed.

Processing logic constructs a model of the user form the captured 3D data (processing block 304). In embodiments, the model is constructed from the 3D data of the user performing the activity. Furthermore, the model may be constructed from the 3D data captured by the depth mapping capture system, 3D data received from another capture system, one or more additional motions sensors, or a combination thereof. As discussed herein, the model is a skeletal model of the user, which has nodes/points associated with the location of joints of a user. In embodiments, the skeletal model can include 24 nodes/points representing different joints, such as ankles, knees, hips, shoulder, wrists, elbows, etc. of the user.

Processing logic tracks the model of the user in the 3D data (processing block 306). Processing logic utilizes the constructed skeletal model, the nodes/points defined by the model, and the user data within the three-dimensional data captured over a period of time to detect movement of those nodes/points over a period of time within the captured three-dimensional data. The collection of movements of the different points represents movement of the user's model, and thus the user, over the period of time.

Processing logic logs the motion data for the model (processing block 308). In embodiments, each node/point in the model may be tracked and associated with a series of (x, y, z, t) coordinates that provide a spatial (x, y, z) and a temporal (t) location of that point. The series of coordinates for each node/point tracked in the 3D image data, and the difference there between provide the motion of each node/point in the model over time. The collected motion of the points therefore provides the motion of the model over time, and is indicative of the captured user's movements.

Processing logic reports the motion log to a motion assessment system (processing block 310). In embodiments, the reporting of one or more motion log(s) occurs on a periodic basis. However, the motion log(s) may also be reported when a specific duration of user motion has been captured, based on a request of the motion assessment system, as well as other conditions.

Figure 4:
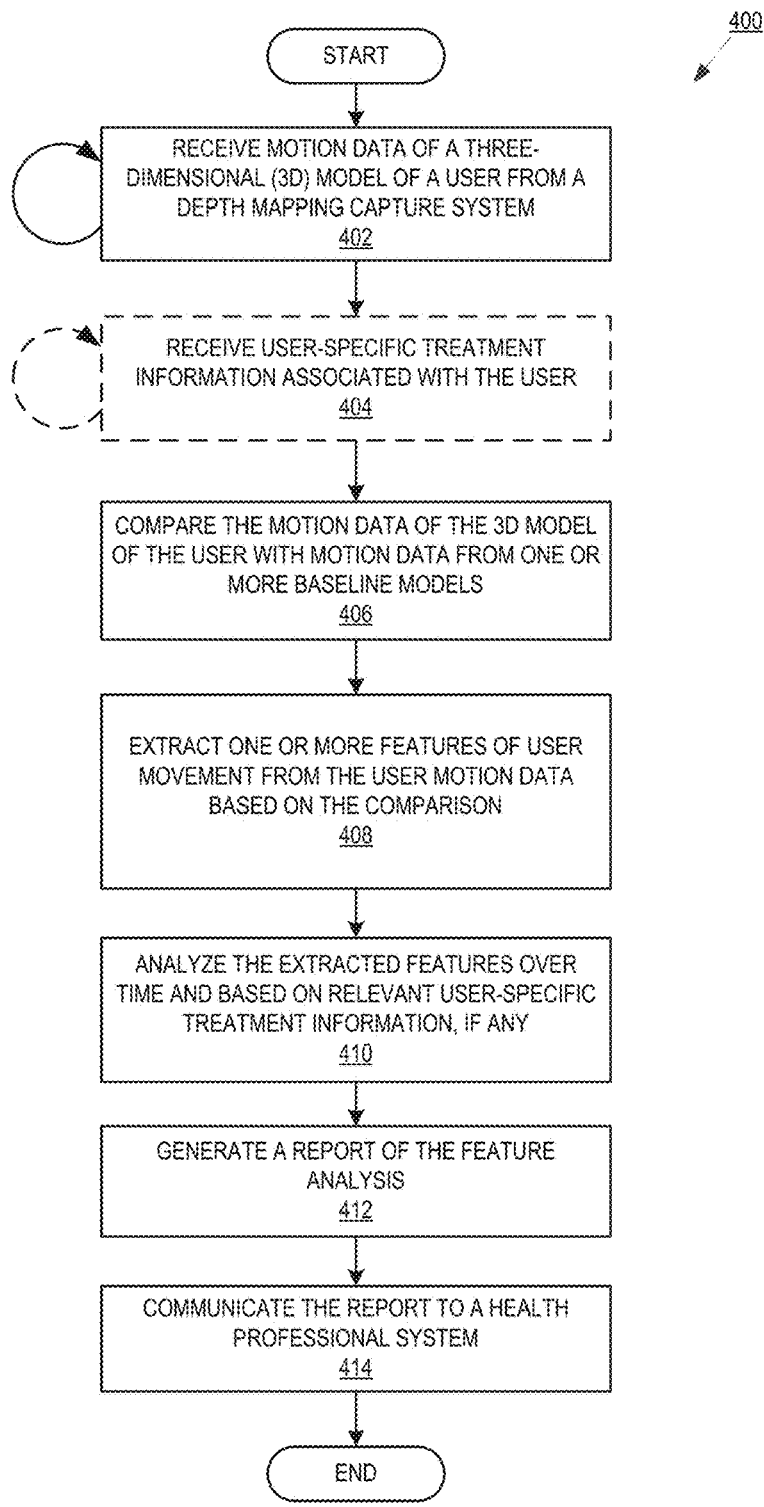
FIG. 4 is a flow chart illustrating a process for analyzing motion data for medical treatment and diagnosis by a motion analysis system, in accordance with an embodiment of the disclosure.

FIG. 4 is a flow chart illustrating a process 400 for analyzing motion data for medical treatment and diagnosis by a motion analysis system, in accordance with an embodiment of the disclosure. The process is performed by processing logic that may comprise hardware (circuitry, dedicated logic, etc.), software (such as is run on a general purpose computer system or a dedicated machine), firmware, or a combination. In embodiments, the process is performed by a motion assessment system (e.g., motion assessment system 130 or 250).

Referring to FIG. 4, processing logic begins receiving motion data of a three-dimensional (3D) model of a user from a depth mapping capture system (processing block 402). In embodiments, the motion data includes a skeletal model constructed by the depth mapping capture system in accordance with the discussion above. However, in some embodiments, the processing logic of FIG. 4 may receive only motion data (e.g. raw signal data captured by a depth mapping capture system) and perform the model construction in response to receipt of 3D motion data, as discussed above. Processing logic may also perform additional operations on the motion data, such as applying one or more filters (e.g., a low pass filter to clean up high frequency signal noise), to the raw signal data prior to model construction.

In embodiments, processing logic also receives optional user-specific treatment information associated with the user (processing block 404). As discussed herein, the user-specific treatment information can include information received from a health professional system indicative of a previous diagnosis, medication prescription, medication change, physical therapy, etc. In embodiments, a user may provide their own information relevant to treatment or diagnosis, such as user detected freezing, falling, etc., to processing logic.

Processing logic compares the motion data of the 3D model of the user with motion data from one or more baseline models (processing block 406). As discussed herein, different types of baseline models may be used by processing logic, including motion of models from healthy individuals, motion of models from individuals diagnosed with specific conditions, machine learning motion models trained using the motions of one or more people known to have a chronic neurodegenerative or musculoskeletal disease, and previously captured motions of the user's skeletal model.

Processing logic extracts one or more features of user movement from the user motion data (processing block 408). In embodiments, as discussed herein, the features may be extracted directly from the motion of the user's skeletal model (e.g., detected freezing, falling, gait, posture, stride frequency, stride length, balance, etc.), as well as based on the comparison to motion of one or more of the baseline models. For example, the extracted motion features can include mean timing and range of one or more motions (e.g., sit to stand time, walking velocity, etc.), mean timing and range across movement repetitions, joint angles during certain motions (e.g., elbow angle or rotation), body/postural sway (e.g., trunk sway, spine angle sway, etc.), distances of certain movements (e.g., stride length), etc., which are extracted by processing logic from the captured user motion data.

In embodiments, coordination between one or more of the extracted motion features may also be determined by processing logic. Coordination can be relevant to diagnosis of a chronic neurodegenerative disease. For example, there is strong evidence that patients suffering from a chronic neurodegenerative disease will exhibit their upper body (e.g., trunk) and lower extremities rotating together about their ankle joints, referred to herein as the ankle strategy. Healthy patients, however, exhibit movements where the upper body and lower body move in opposite directions (referred to as the hip strategy), make transitions between the hip strategy and the ankle strategy, and modulate the two co-existing strategies. In embodiments, processing logic can extract various user motions based on this knowledge of hip and ankle strategies to detect or diagnose a chronic neurodegenerative disease, which is discussed in greater detail below.

Processing logic analyzes the extracted features over time and based on relevant user-specific data, if any (processing block 410). In embodiments, the extracted features correspond with similar features of the motion models. Processing logic looks to the similarity of the feature from the user model movement with movement in the motion model to detect when a match occurs. Based on the similarity with one or more motion models with the detected motions, processing logic can compute a risk score associated with the likelihood of having a potential chronic neurodegenerative or musculoskeletal medical condition. For example, a risk score can be based on a test for similarity between motion features from a machine learning model trained by people having a specific condition with the motion feature extracted from the user's model.

In embodiments, each motion model is associated with one or more medical conditions, detection of the similarity is indicative of existence of the condition, and detection of a degree of similarity with one or more models can be indicative of a risk of user having or developing a chronic neurodegenerative or musculoskeletal medical condition. Furthermore, tracking of the feature over time can identify when severity of a motion feature (e.g., tremor) is increasing or decreasing, how it is affected in different interaction scenarios, how it is responding to a new medical treatment, rates of fatigue, impact of specific motions on a user's posture, detecting certain events that precede a fall, etc. Each of these detections can effect a computed risk score in order to adapt a risk score to new or evolving conditions experienced by a user, such as increasing a risk score as tremor motions increase, increasing a risk score as movement strategies discussed in greater detail herein change, decreasing a risk score in response to noticing certain triggers unrelated to a chronic neurodegenerative or musculoskeletal medical condition, as well as other factors that could change or otherwise alter a computed risk score.

Continuing the example above, processing logic can additionally analyze the extracted features to assess coordination between a user's upper and lower body (e.g., sway of user's trunk $\alpha_{trunk}$ relative to their knees $\alpha_{knee}$) to determine timing, preference, and use of the ankle or hip strategies. In embodiments, processing logic analyzes the coordination between the upper and lower body, which can be assessed by a covariance index ($CI_\alpha \in [-1,1]$) between the trunk and the knee, defined as the covariance of the motions of a user's trunk, $\alpha_{trunk}$, and motions of a user's knee, $\alpha_{knee}$, normalized by the standard deviations of the signals associated with those motions. In embodiments, a positive $CI_\alpha$ indicates that the motions (upper body and lower body motions) are in-phase, which is associated with the ankle strategy. A negative $CI_\alpha$ indicates counter-phase motions, and that the subject was using hip strategy to maintain body balancing. To calculate a postural strategy index (PSI) indicating which strategy (e.g., ankle or hip) was used, a threshold can be set, such as ±0.4, to distinguish between in-phase and counter-phase motion patterns. In embodiments, a postural strategy index (PSI) value can be calculated based on user motions by processing logic calculating $$PSI = \left(\frac{T_{IP} - T_{CP}}{T}\right),$$

where $T_{IP}$ is the time spent in in-phase motion patterns, $T_{CP}$ is the time spent in counter-phase motion patterns, and T is the time of the testing (e.g., time in which motion data is captured by a depth mapping capture system). Analysis of motions of a user having a chronic neurodegenerative or musculoskeletal disease, for example, indicate that the sway of the user's trunk and knee together in an anterior-posterior direction along a sagittal plane will exhibit a strong in-phase pattern, indicating an ankle strategy during standing motions. This in-phase pattern can be confirmed by processing logic calculating the covariance index and PSI values for motions during a time of assessment. When the calculated covariance index is mostly greater than the threshold (e.g., ±0.4) during the time period of a standing motion, and calculated PSI values will also exceed a threshold, and processing logic can predict that the user may be suffering from a chronic neurodegenerative or musculoskeletal disease (e.g., Parkinson's Disease, Multiple Sclerosis, etc.). Healthy users, however, that tend to use the hip strategy will exhibit PSI values distributed around zero for similar motions, and processing logic can accordingly predict that the user does not suffer from a chronic neurodegenerative or musculoskeletal disease.

Processing logic utilizes the analysis results to generate a report (processing block 412) and communicate the report to a health professional system (processing block 414). As discussed herein, the reports may include an assessment of the user's fall or freezing risk based on detected motion features, frequency of occurrence of detected features, usage of different strategies for body balancing, quantitative analysis of the strategies used, etc. In embodiments, the reports may also include an indication of any new detected conditions, assessment of ongoing/modified treatments, indication of a specific detected motion (e.g., a fall), as well as other detected motions or associated conditions. In embodiments, the reports may also include an adaptive risk score computed based on one or more motion features, trend analysis, detected new conditions, medication intervention strategies, as well as other information detected by processing logic that would be useful to a medical professional treating or diagnosing a user with a potential chronic neurodegenerative or musculoskeletal medical condition. In embodiments, the risk score can be generated by processing logic in real time in response to tracking movements of the model of the user, and optionally the reports generated in response to the real time risk score having a value above a threshold. Furthermore, as discussed herein, the reports can include visualizations that enable a health professional to replay user motions, compare user options to model motions, select among different medical treatment events (e.g., starting medications, changing dosages, stopping medication, selecting different therapies, starting a course of neural stimulation, etc.) and view a risk score adapted to a selected medical treatment event, and selectively apply different motion and quantitative visualizations when assessing whether a user has a chronic neurodegenerative or musculoskeletal disease.

Figure 5:
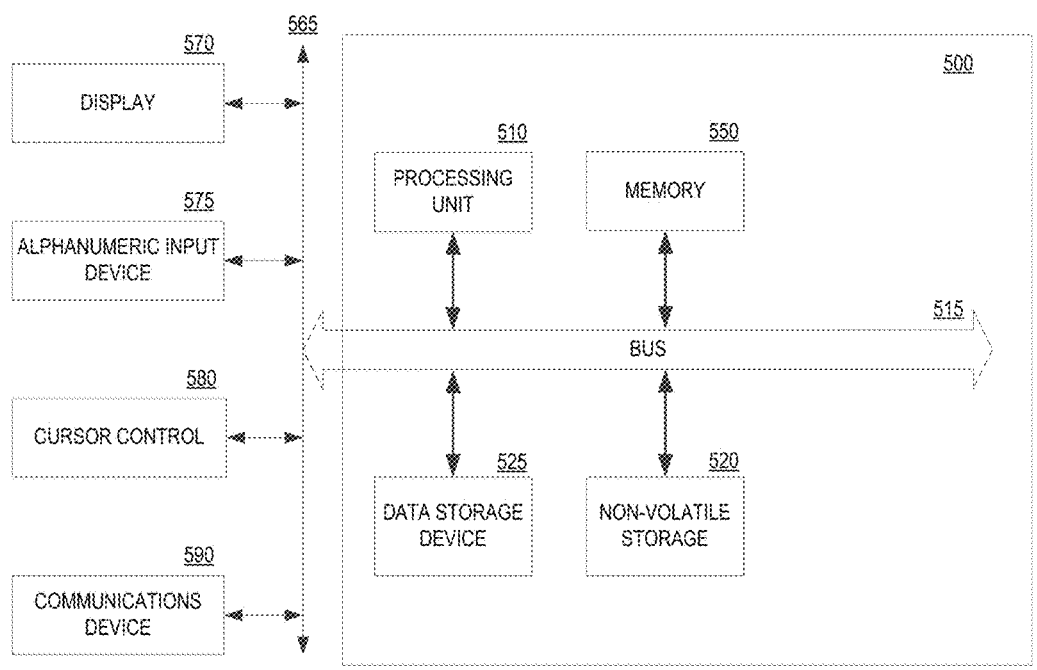
FIG. 5 is an exemplary computer system that may be used with the embodiments discussed herein.

FIG. 5 is an exemplary computer system that may be used with the embodiments discussed herein. It will be apparent to those of ordinary skill in the art, however that other alternative systems of various system architectures may also be used.

The data processing system illustrated in FIG. 5 includes a bus or other internal communication means 515 for communicating information, and a processor 510 coupled to the bus 515 for processing information. The system further comprises a random access memory (RAM) or other volatile storage device 550 (referred to as memory), coupled to bus 515 for storing information and instructions to be executed by processor 510. Main memory 550 also may be used for storing temporary variables or other intermediate information during execution of instructions by processor 510. The system also comprises a read only memory (ROM) or static storage device 520 coupled to bus 515 for storing static information and instructions for processor 510, and a data storage device 525 such as a magnetic disk or optical disk and its corresponding disk drive. Data storage device 525 is coupled to bus 515 for storing information and instructions.

The system may further be coupled to a display device 570, such as a cathode ray tube (CRT), a liquid crystal display (LCD), or other display device coupled to bus 515 through bus 565 for displaying information to a computer user. An alphanumeric input device 575, including alphanumeric and other keys, may also be coupled to bus 515 through bus 565 for communicating information and command selections to processor 510. An additional user input device is cursor control device 580, such as a mouse, a trackball, stylus, or cursor direction keys coupled to bus 515 through bus 565 for communicating direction information and command selections to processor 510, and for controlling cursor movement on display device 570.

Another device, which may optionally be coupled to computer system 500, is a communication device 590 for accessing other nodes of a distributed system via a network. The communication device 590 may include any of a number of commercially available networking peripheral devices such as those used for coupling to an Ethernet, token ring, Internet, or wide area network. The communication device 590 may further be a null-modem connection, or any other mechanism that provides connectivity between the computer system 500 and the outside world. Note that any or all of the components of this system illustrated in FIG. 5 and associated hardware may be used in various embodiments.

It will be appreciated by those of ordinary skill in the art that any configuration of the system may be used for various purposes according to the particular implementation. The control logic or software implementing the embodiments can be stored in main memory 550, mass storage device 525, or other storage medium locally or remotely accessible to processor 510.

It will be apparent to those of ordinary skill in the art that the system, method, and process described herein can be implemented as software stored in main memory 550 or read only memory 520 and executed by processor 510. This control logic or software may also be resident on an article of manufacture comprising a computer readable medium having computer readable program code embodied therein and being readable by the mass storage device 525 and for causing the processor 510 to operate in accordance with the methods and teachings herein.

The embodiments discussed herein may also be embodied in a handheld or portable device containing a subset of the computer hardware components described above. For example, the handheld device may be configured to contain only the bus 515, the processor 510, and memory 550 or 525. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of embodiments for such a device would be apparent to one of ordinary skill in the art given the disclosure as provided herein.

The embodiments discussed herein may also be embodied in a special purpose appliance including a subset of the computer hardware components described above. For example, the appliance may include a processor 510, a data storage device 525, a bus 515, and memory 550, and only rudimentary communications mechanisms, such as a small touch-screen that permits the user to communicate in a basic manner with the device. In general, the more special-purpose the device is, the fewer of the elements need be present for the device to function.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments, including what is described in the Abstract, is not intended to be exhaustive or limiting to the precise forms disclosed. While specific embodiments, and examples, are described herein for illustrative purposes, various modifications are possible within the scope of the discussion herein, as those skilled in the relevant art will recognize.

These modifications can be made in light of the above detailed description. The terms used in the following claims should not be construed to limit the discussion to the specific embodiments disclosed in the specification. Rather, the scope is to be determined entirely by the following claims, which are to be construed in accordance with established doctrines of claim interpretation.

What is claimed is:

1. A method comprising:
constructing, with a computer processing system, a model of a target person from three-dimensional (3D) image data of the target person performing an activity over a period of time;
tracking, with a computer processing system, movement of the model of the target person in the 3D image data over the period of time;
detecting one or more motion features in the movement of the model of the target person that are relevant to diagnosis, treatment, care, or any combination thereof, of a potential chronic neurodegenerative or musculoskeletal medical condition; and
computing a risk score associated with a likelihood of the target person having the medical condition based on the detected motion features,
wherein the risk score is computed based on a comparison of similarity between one or more tracked motions of the target person with one or more motions of a baseline model, a comparison of similarity between one or more tracked motions of the target person with one or more prior corresponding tracked motions of the target person, a comparison of one or more tracked motions of the target person with one or more thresholds established from corresponding healthy motions, data indicative of the target person starting a medication, data indicative of the target person ending a medication, data indicative of the target person changing a medication dosage, data indicative of the target person participating in physical therapy, data indicative of the target person undergoing neural stimulation, or any combination thereof.

2. The method of claim 1, further comprising:
training a machine learning model based on movement features of people with a known chronic neurodegenerative or musculoskeletal medical condition; and
testing the motion features of the target person against the machine learning model to compute the risk score associated with the likelihood of the target person having the medical condition.

3. The method of claim 1, wherein the risk score is computed in real-time in response to tracking the movement of the model of the target person.

4. The method of claim 1, further comprising:
capturing 3D image data with a depth mapping sensor, wherein the 3D image data is captured when the target person is within a field of view of the depth mapping sensor, during a specific time period, when the model of movement of the target person is indicative of a predefined task, or a combination thereof.

5. The method of claim 1, wherein the model comprises three dimensional location data indicative of a plurality of different points on a body of the target person, and the movement of the model comprises movement of the points in space over the period of time, movement of the points relative to one another over the period of time, or any combination thereof.

6. The method of claim 1, wherein the activity is performed by the target person outside of a medical diagnosis context.

7. The method of claim 1, further comprising:
detecting a treatment event;
measuring a response to the treatment by the target user; and
adjusting a computation of the risk score responsive to the measured response to the treatment.

8. The method of claim 7, the computation of the risk score is adjusted by one or more of adjusting one or more motion characteristic thresholds, changing a machine learning model from which the motions of the model of the target user are compared and the risk score is computed, changing coefficients or parameters of the risk score computation to account for the treatment event, changing coefficients or parameters of the risk score computation based on the measured response to the treatment event, or any combination thereof.

9. The method of claim 1, further comprising:
generating a report that comprises the one or more motion features detected in the movement of the model of the target person; and
transmitting the report to a health professional system associated with a health professional.

10. The method of claim 9, further comprising:
receiving treatment data inputted by the health professional system, the treatment data comprising one or more of data indicative of medication type, medication dosage, physical therapy, and neural stimulation;
detecting one or more motion features in movement of a second model of the target person over a second period of time; and
detecting a trend in motion features based on a comparison of the model with the second model; and
generating a second report that correlates the treatment data with the detected trend in motion features.

11. The method of claim 9, wherein the report comprises a visualization of the motion of the target person over the period of time.

12. The method of claim 1, further comprising:
capturing additional target person motion data with a second device while the target person is performing the activity, wherein the additional motion data comprises timing data;
correlating the additional target person motion data with the 3D image data based on the timing data to generate a combined motion data; and
constructing the model of the target person from the combined motion data.

13. The method of claim 12, wherein the second device is a wearable device worn by the target person while the target person is performing the activity.

14. The method of claim 13, wherein the model is a skeletal model of the target person, and the plurality of different points comprise points representing different joints of the target person.

15. The method of claim 1, wherein the detecting further comprises:
comparing the movement of the constructed model of the target person with movement of one or more baseline models, wherein each baseline model is a representation of movements relevant to diagnosis, treatment, care, or any combination thereof, of a potential chronic neurodegenerative or musculoskeletal medical condition of the target person; and
detecting the one or more motion features based on the comparison of the movement of the constructed model of the target person with the movement of one or more baseline models.

16. The method of claim 15, wherein the one or more baseline models comprise one or more of a healthy baseline model generated from movement of one or more people who have not been diagnosed with a chronic neurodegenerative or musculoskeletal disease, a condition specific baseline model generated from movement of one or more people that have been diagnosed with a specific chronic neurodegenerative or musculoskeletal disease, and a historical baseline model generated from movement of the target person prior to the period of time.

17. The method of claim 16, wherein the detected one or more motion features comprise a freezing motion, falling motion, gait motion, target person posture during one or more tracked movements, stride frequency, stride length, one or more motions indicative of balance of the target person over the period of time, or any combination thereof.

18. A non-transitory machine readable storage medium having instructions stored thereon, which when executed by a processing system, cause the processing system to perform a method comprising:
constructing, with a computer processing system, a model of a target person from three-dimensional (3D) data of the target person performing an activity over a period of time;
tracking, with a computer processing system, movement of the model of the target person in the 3D data over the period of time;
detecting one or more motion features in the movement of the model of the target person that are relevant to diagnosis, treatment, care, or any combination thereof, of a potential chronic neurodegenerative or musculoskeletal medical condition; and
computing a risk score associated with likelihood of the target person having the medical condition based on the detected motion features,
wherein the risk score is computed based on a comparison of similarity between one or more tracked motions of the target person with one or more motions of a baseline model, a comparison of similarity between one or more tracked motions of the target person with one or more prior corresponding tracked motions of the target person, a comparison of one or more tracked motions of the target person with one or more thresholds established from corresponding healthy motions, data indicative of the target person starting a medication, data indicative of the target person ending a medication, data indicative of the target person changing a medication dosage, data indicative of the target person participating in physical therapy, data indicative of the target person undergoing neural stimulation, or any combination thereof.

19. The non-transitory machine readable storage medium of claim 18, wherein the detecting further comprises:
comparing the movement of the constructed model of the target person with movement of one or more baseline models, wherein each baseline model is a representation of movements relevant to diagnosis, treatment, care, or any combination thereof, of a potential chronic neurodegenerative or musculoskeletal medical condition of the target person; and detecting the one or more motion features based on the comparison of the movement of the constructed model of the target person with movement of one or more baseline models.

20. The non-transitory machine readable storage medium of claim 18, further comprising:
capturing 3D image data with a depth mapping sensor, wherein the 3D image data is captured when the target person is within a field of view of the depth mapping sensor, during a specific time period, when the model of movement of the target person is indicative of a predefined task, or any combination thereof.

21. The non-transitory machine readable storage medium of claim 18, further comprising:
capturing additional target person motion data with a second device while the target person is performing the activity, wherein the additional motion data comprises timing data;
correlating the additional target person motion data with the 3D data based on the timing data to generate a combined motion data; and
constructing the model of the target person from the combined motion data.

22. The non-transitory machine readable storage medium of claim 18, further comprising:
generating a report that comprises the one or more motion features detected in the movement of the model of the target person; and
transmitting the report to a health professional system associated with a health professional.

23. A method comprising:
constructing, with a computer processing system, a model of a target person from three-dimensional (3D) image data of the target person performing an activity over a period of time;
tracking, with a computer processing system, movement of the model of the target person in the 3D image data over the period of time;
detecting one or more motion features in the movement of the model of the target person that are relevant to diagnosis, treatment, care, or any combination thereof, of a potential chronic neurodegenerative or musculoskeletal medical condition;
computing a risk score associated with a likelihood of the target person having the medical condition based on the detected motion features;
receiving treatment data comprising one or more of data indicative of medication type, medication dosage, physical therapy, and neural stimulation;
detecting one or more motion features in movement of a second model of the target person over a second period of time;
detecting a trend in motion features based on a comparison of the model with the second model; and
generating a report that correlates the treatment data with the detected trend in motion features.

* * * * *